(12) United States Patent
Wagman (10) Patent No.: US 6,979,354 B2
(45) Date of Patent: Dec. 27, 2005

(54) PROSTHETIC ATTACHMENT LOCKING DEVICE

(75) Inventor: Chris L. Wagman, Red Lion, PA (US)

(73) Assignee: Wagman Manufacturing, Inc., Manchester, PA (US)

( * ) Notice: Subject to any disclaimer, the term of this patent is extended or adjusted under 35 U.S.C. 154(b) by 174 days.

(21) Appl. No.: 10/428,548

(22) Filed: May 2, 2003

(65) Prior Publication Data

US 2004/0030410 A1     Feb. 12, 2004

Related U.S. Application Data

(60) Provisional application No. 60/377,726, filed on May 3, 2002.

(51) Int. Cl.[7] ................................................ A61F 2/60
(52) U.S. Cl. ...................................................... 623/33
(58) Field of Search ............................. 623/33, 34, 35, 623/36, 37, 38; 606/218; 70/DIG. 9; 74/575; 269/212; 403/105, 152, DIG. 4

(56) References Cited

U.S. PATENT DOCUMENTS

| | | | |
|---|---|---|---|
| 4,842,009 A | * | 6/1989 | Reback .................. 137/315.15 |
| 5,040,652 A | * | 8/1991 | Fish et al. ..................... 70/189 |
| 5,526,918 A | * | 6/1996 | Dullighan et al. .......... 194/317 |
| 6,267,787 B1 | * | 7/2001 | Capper et al. ................. 623/36 |
| 6,605,118 B2 | * | 8/2003 | Capper et al. ................. 623/36 |
| 6,689,171 B2 | * | 2/2004 | Slemker et al. ............... 623/33 |

* cited by examiner

Primary Examiner—David J. Isabella
Assistant Examiner—Thomas J. Sweet
(74) Attorney, Agent, or Firm—Barley Snyder LLC (57) ABSTRACT

A prosthetic attachment locking device includes a body and a releasing mechanism. The body has an axial hole that extends from a first surface to an opposing second surface, and a pawl receiving recess that communicates with the axial hole. The releasing mechanism has a central axle with a pawl that is received in the pawl receiving recess. The central axle has a clutch bearing that rotates the pawl in a first direction when an attachment pin is inserted into the axial hole. The clutch bearing secures the attachment pin in the body and is reversible such that an attachment pin can be inserted from the first surface or the second surface of the body. Because the prosthetic attachment locking device is reversible, the releasing mechanism can be positioned to project toward an interior of a residual limb whether used on a right-side residual limb or a left-side residual limb.

21 Claims, 11 Drawing Sheets

PROSTHETIC ATTACHMENT LOCKING DEVICE

CROSS-REFERENCE TO RELATED APPLICATIONS

This application claims the benefit of U.S. Provisional Application Ser. No. 60/377,726, filed May 3, 2002.

FIELD OF THE INVENTION

The invention relates to a prosthetic attachment locking device and, more specifically, to a prosthetic attachment locking device having a reversible releasing mechanism that enables the releasing mechanism to always project toward an interior of a residual limb.

BACKGROUND OF THE INVENTION

Prosthetic attachment locking devices are used to secure a patient's residual limb, which is fitted in a prosthetic socket, to a pylon of a prosthetic limb. The prosthetic attachment locking device typically includes a body having an axial hole extending therethrough and a releasing mechanism having a spring loaded reciprocating pawl that cooperates with the axial hole. The prosthetic socket is attached to a first surface of the body by fasteners such as screws that are received through a plurality of through-holes. A ratcheted attachment pin that extends from a distal end of a liner positioned on the patient's residual limb is inserted through the prosthetic socket and through the axial hole of the prosthetic attachment locking device until a distal end of the attachment pin is received in the pylon of the prosthetic limb. The attachment pin is secured in the prosthetic attachment locking device by the pawl that engages the teeth of the attachment pin. The pawl rotates in only one direction, so that the attachment pin may be inserted into the axial hole, but not removed therefrom. To release the attachment pin from the prosthetic attachment locking device, the release mechanism displaces the pawl from the axial hole so that the patient can pull-out the attachment pin and remove the residual limb from the prosthetic limb.

In these devices, it is preferable that the release mechanism projects from the body of the prosthetic attachment locking device toward the interior of the residual limb for comfort and accessibility. Because the pawl only rotates in one direction, a prosthetic attachment locking device that has a releasing mechanism projecting toward the interior of a left-side residual limb is incapable of being used on a right-side residual limb in a way that enables the releasing mechanism to project toward the interior of the right-side residual limb. Similarly, a prosthetic attachment locking device that has a releasing mechanism projecting toward the interior of a right-side residual limb is incapable of being used on a left-side residual limb in a way that enables the releasing mechanism to project toward the interior of the left-side residual limb. It is therefore necessary to manufacture prosthetic attachment locking devices having different designs to accommodate either a right-side residual limb or a left-side residual limb.

In these devices, it is also preferable that the release mechanism, especially the pawl, is prevented from moving with respect to the attachment pin in order to prevent the attachment pin from loosening from its attached state in the prosthetic attachment locking device. Because many prosthetic attachment locking devices do not contain locking means for the releasing mechanism or are merely threaded into the body, the fastening mechanism becomes loose and resultantly weakens the attachment of the attachment pin to the prosthetic attachment locking device. Further, many prosthetic attachment locking devices merely use through-holes and an attachment means such as screws to fasten the body to the prosthetic socket. Because the attachment surface of the prosthetic socket is grinded during manufacturing, the socket surface is often irregular. The through-holes in the body are not manufactured to evenly distribute torque caused by the irregular socket surface causing the prosthetic socket to become uneven and uncomfortable to the patient.

It is therefore desirable to develop a prosthetic attachment locking device that is reversible in that the releasing mechanism will project toward the interior of the residual limb whether used on a right-side residual limb or a left-side residual limb enabling versatility and decreasing manufacturing costs. It is also desirable to provide a prosthetic attachment locking device whereby the releasing mechanism is maintained in an attached state, and the prosthetic socket evenly distributes torque to increase patient comfort.

SUMMARY OF THE INVENTION

The invention relates to a prosthetic attachment locking device. The device includes a body and a releasing mechanism. The body has an axial hole that extends from a first surface to an opposing second surface. The body has a first side with a pawl receiving recess that communicates with the axial hole. The releasing mechanism has a central axle with a pawl that is received in the pawl receiving recess. The central axle has a clutch bearing that rotates the pawl in a first direction when an attachment pin is inserted into the axial hole and engages the pawl. The clutch bearing secures the attachment pin in the body and is reversible such that an attachment pin can be inserted from the first surface or the second surface of the body.

BRIEF DESCRIPTION OF THE DRAWINGS

FIG. 10 shows a releasing button of the prosthetic attachment locking device.

FIG. 11 shows the releasing button of the prosthetic attachment locking device.

FIG. 12 shows a bushing of the prosthetic attachment locking prosthetic attachment locking device.

FIG. 13 shows a cover of the prosthetic attachment locking device.

FIG. 16 shows a ball plunger of the prosthetic attachment locking device.

FIG. 17 shows a clutch bearing of the prosthetic attachment locking device.

FIG. 18 shows a sleeve of the prosthetic attachment locking device.

FIG. 19 shows a hollow cylindrical spacer.

DETAILED DESCRIPTION OF THE INVENTION

FIGS. 1–6 show a prosthetic attachment locking device 10 having an essentially rectangular body 11, a releasing mechanism 12 and a ratcheted attachment pin 13. The body 11, the releasing mechanism 12, and the attachment pin 13 are preferably made from a material such as a high strength aluminum alloy for light weight and durability. The individual elements of the prosthetic attachment locking device 10 and assembly and attachment of the prosthetic attachment locking device 10 will be described in greater detail herein.

Figure 1:
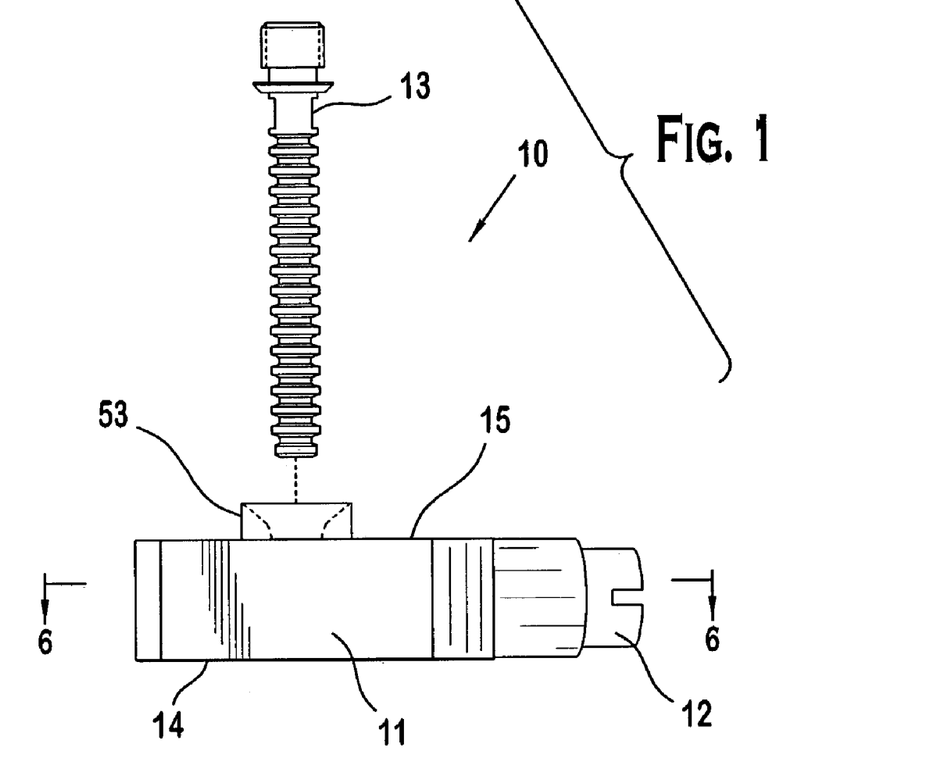
FIG. 1 is a front schematic view of a prosthetic attachment locking device and an attachment pin before insertion of the attachment pin for attachment with a right-side residual limb.
Figure 3:
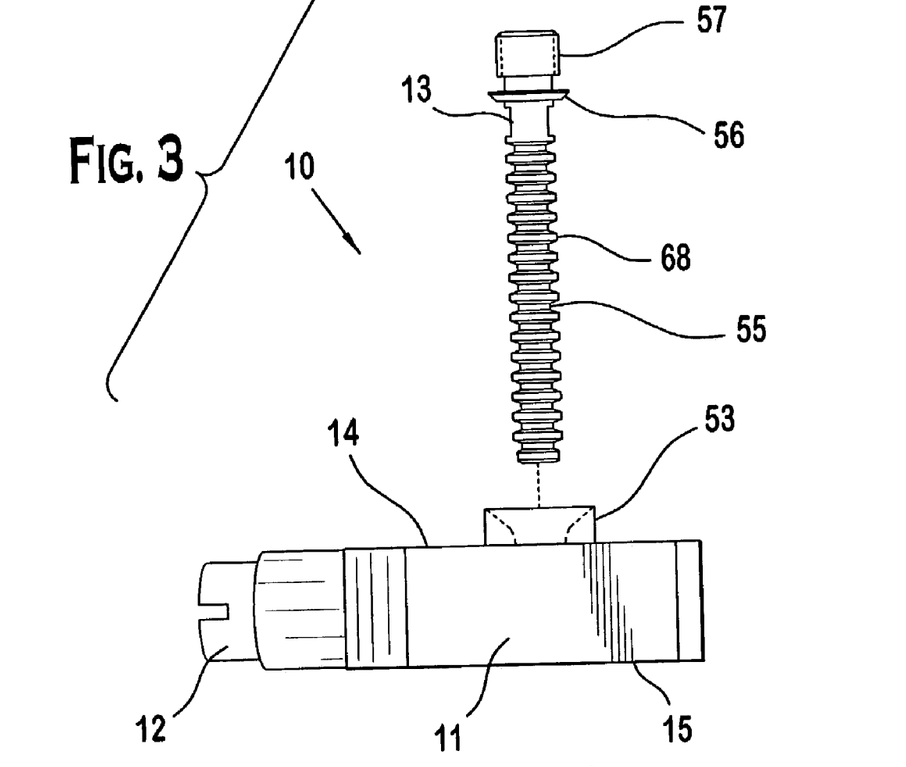
FIG. 3 is a front schematic view of the prosthetic attachment locking device and the attachment pin before insertion of the attachment pin for attachment with a left-side residual limb.
Figure 7:
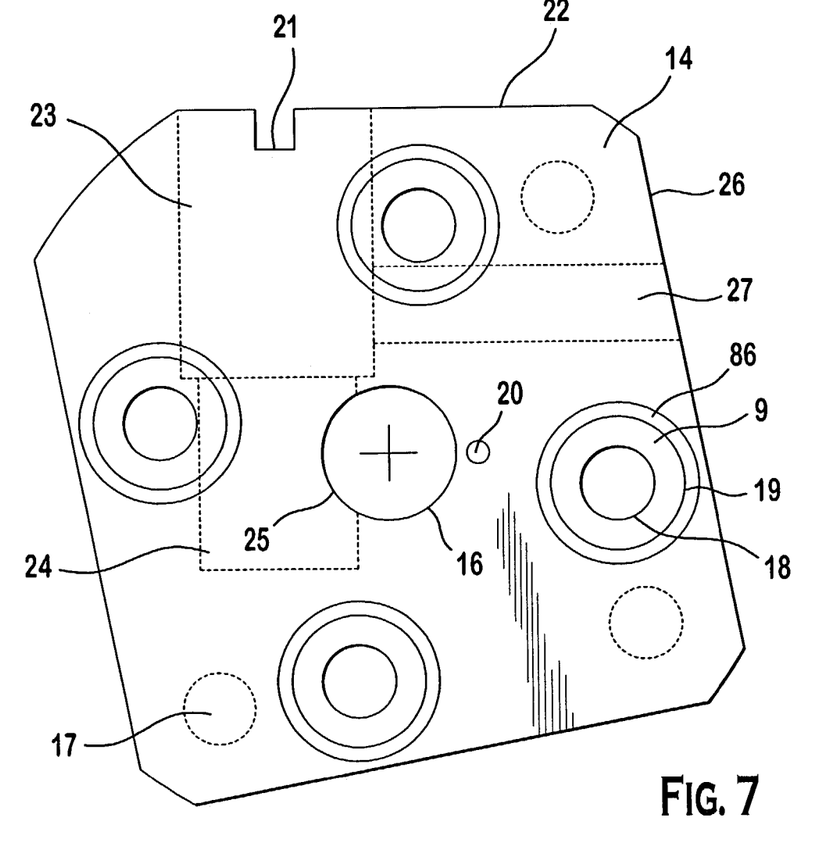
FIG. 7 is a top plan view of a body of the prosthetic attachment locking device.

As shown in FIGS. 1 and 3, the body 11 has opposing first and second surfaces 14, 15, respectively, that are essentially flat and arranged essentially parallel to each other. The first and second surfaces 14, 15 of the body 11 are of identical configuration and as such only the first surface 14 of the body will be described in greater detail herein. As shown in FIG. 7, the first surface 14 has an axial hole 16, and a first and second set of apertures 17, 18. The axial hole 16 is arranged in an approximate center of the body 11 and extends from the first surface 14 to the second surface 15. The first set of apertures 17 extends from the first surface 14 to the second surface 15. The first set of apertures 17 are threaded and form a universal pattern for attachment of the prosthetic attachment locking device 10 to a pylon 80 of a prosthetic limb 81 by a fastening means (not shown) such as a screw. The second set of apertures 18 extends from the first surface 14 to the second surface 15. Each of the second set of apertures 18 has a hollow cylinder receiving recesses 19. The hollow cylinder receiving recesses 19 are formed on the first surface 14 and the second surface 15 and have a diameter larger than each of the second set of apertures 18 such that the hollow cylinder receiving recesses 19 surround each of the second set of apertures 18. The hollow cylinder receiving recesses 19 have an essentially flat bottom surface 9. A top of the hollow cylinder receiving recesses 19 has a beveled edge 86 to facilitate entry of hollow cylindrical spacers 8, described later, into the hollow cylinder receiving recesses 19. Substantially adjacent to the axial hole 16 and formed on the first surface 14 and the second surface 15 is a dowel pin hole 20. Locking recesses 21 are formed on the first surface 14 and the second surface 15 on a first side 22 of the body 11.

Figure 5:
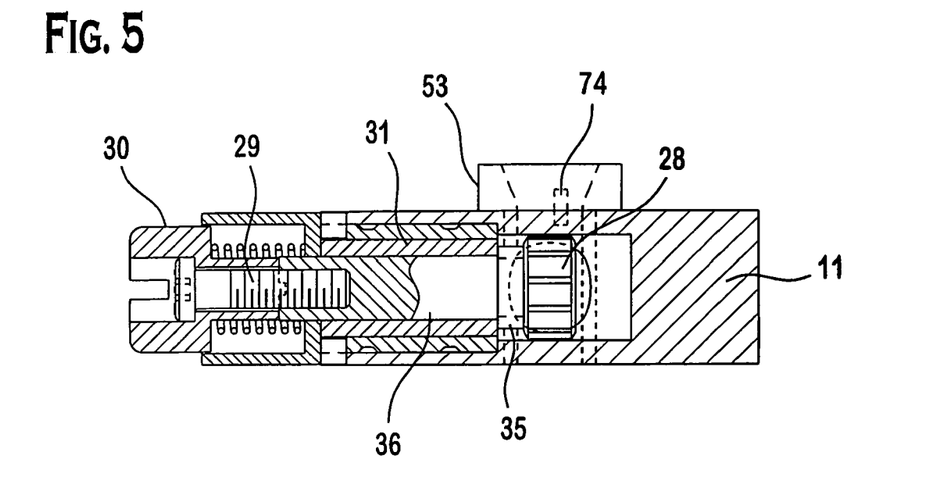
FIG. 5 is a sectional view of the prosthetic attachment locking device of FIG. 4 taken along line 5—5.
Figure 6:
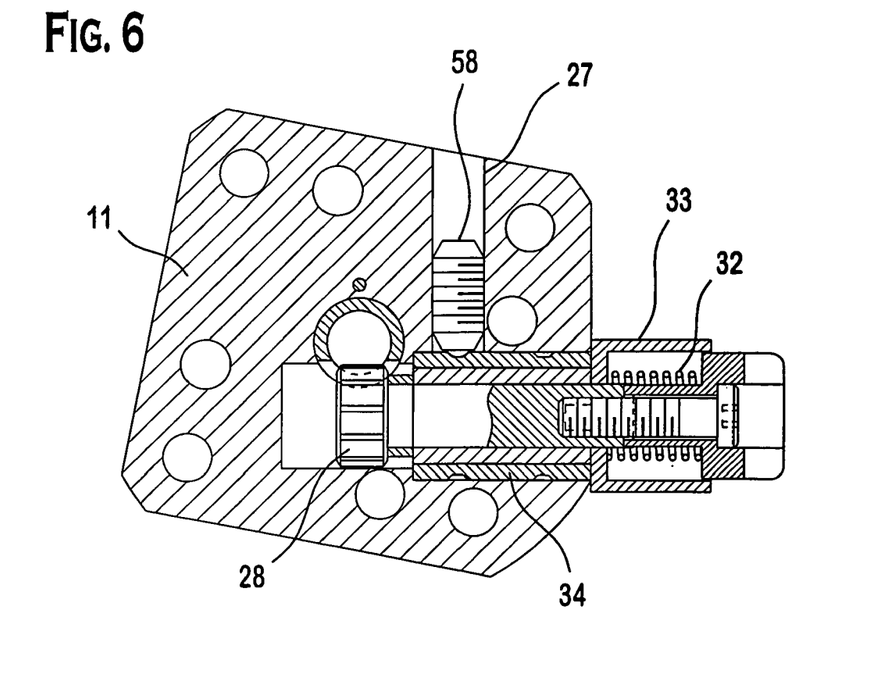
FIG. 6 is a sectional view of the prosthetic attachment locking device of FIG. 1 taken along line 6—6.
Figure 8:
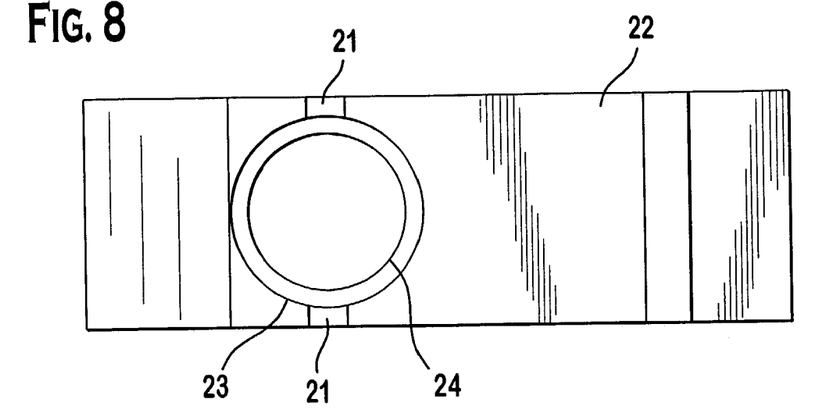
FIG. 8 is a side plan view of the body of the prosthetic attachment locking device.

As shown in FIGS. 7 and 8, adjacent to the locking recesses 21 and extending from the first side 22 of the body 11 toward the axial hole 16, is the sleeve receiving recess 23. Adjacent to the sleeve receiving recess 23 is a pawl receiving recess 24. The pawl receiving recess 24 has a diameter smaller than the sleeve receiving recess 23 and extends toward the axial hole 16. A portion of the pawl receiving recess 24 communicates with the axial hole 16 such that a slot 25 is formed enabling a portion of a pawl 28 to be received in the axial hole 16, as shown in FIGS. 5 and 6. As shown in FIGS. 6 and 7, extending from a second side 26 of the body 11 toward the sleeve receiving recess 23 is a ball plunger receiving recess 27. The ball plunger receiving recess 27 communicates with the sleeve receiving recess 23.

Figure 16A:
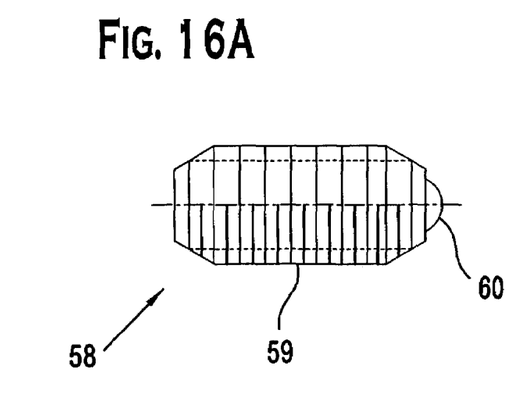
FIG. 16A is a side view of the ball plunger of the prosthetic attachment locking device.
Figure 16B:
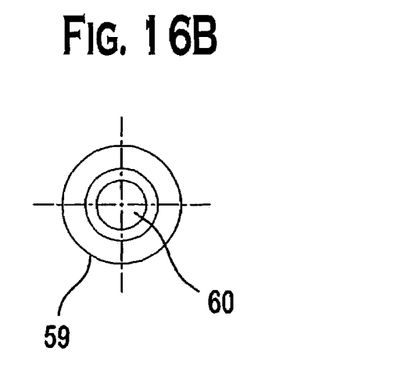
FIG. 16B is a top view of FIG. 16A.

As shown in FIG. 6, the body 11 is provided with a ball plunger 58. The ball plunger 58 has a plunger body 59 housing a ball plunger spring (not shown) and a moveable ball 60, as best shown in FIG. 16. The body 59 is positioned within the ball plunger receiving recess 27 such that the ball 60 projects into the sleeve receiving recess 23 and is biased toward the sleeve receiving recess 23 by the ball plunger spring (not shown). An attachment means such as a screw is received in the body 59 to retain the ball plunger 58 in the ball plunger receiving recess 27.

Figure 12A:
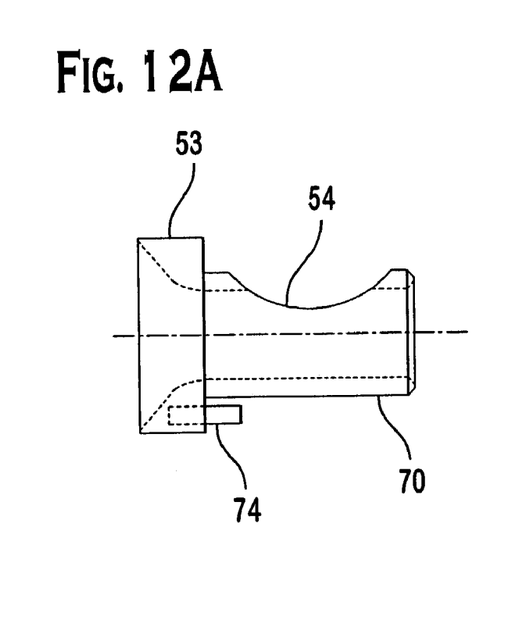
FIG. 12A is a side view of the bushing of the prosthetic attachment locking device.
Figure 12B:
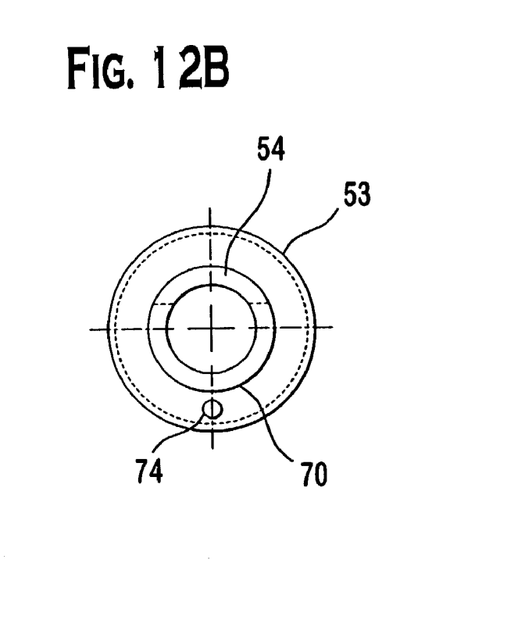
FIG. 12B is a top view of FIG. 12A.

As shown in FIG. 5, the body 11 has a bushing 70. The bushing 70 is removably received in the axial hole 16 and has a radial hole 54 and an outwardly extending flange 53, as best shown in FIG. 12. A dowel pin 74 extends from the flange 53 toward the body 11, as best shown in FIG. 5.

Figure 9:
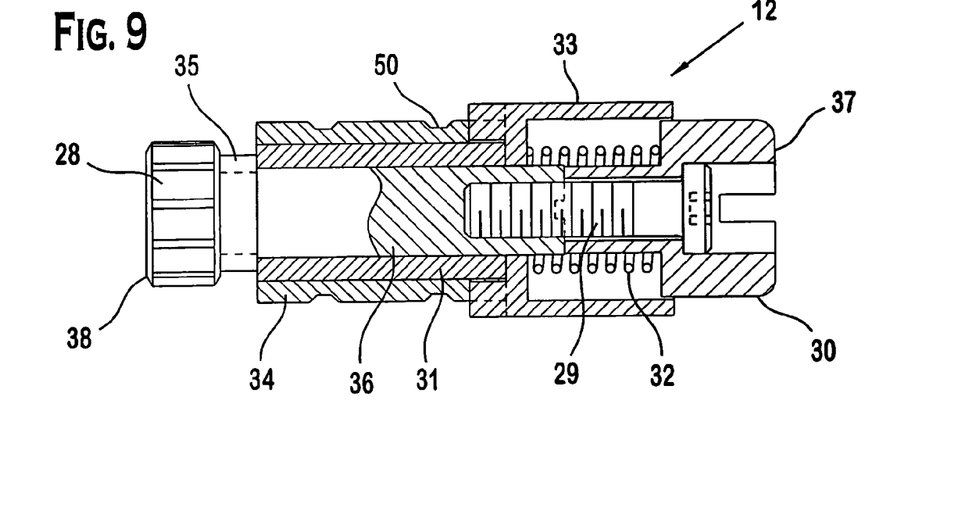
FIG. 9 is a sectional view of a releasing mechanism of the prosthetic attachment locking device.
Figure 10A:
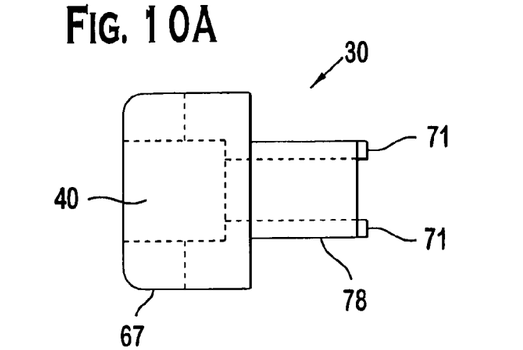
FIG. 10A is a first side view of the releasing button of the prosthetic attachment locking device.
Figure 10B:
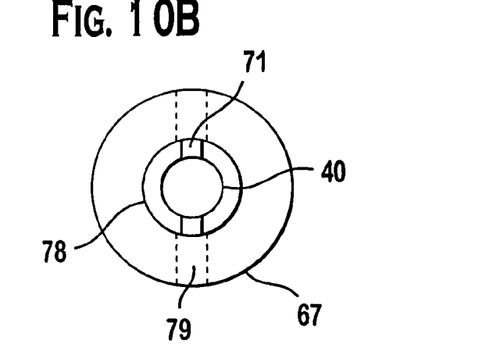
FIG. 10B is a bottom view of FIG. 10A.
Figure 11A:
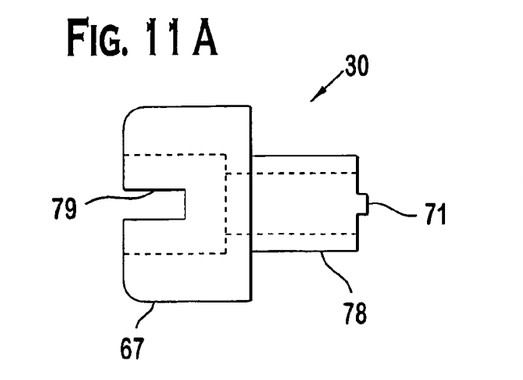
FIG. 11A is a second side view of the releasing button of the prosthetic attachment locking prosthetic attachment locking device.
Figure 11B:
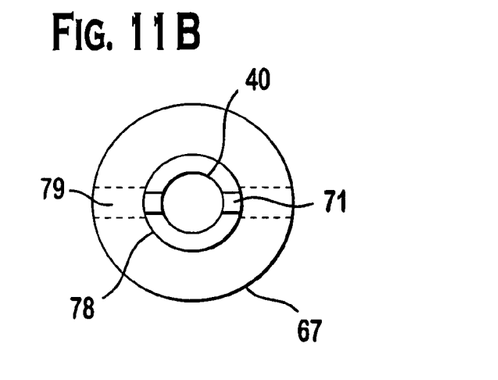
FIG. 11B is a top view of FIG. 11A.

The releasing mechanism 12 will now be described in greater detail. As shown in FIG. 9, the releasing mechanism 12 has a first end 37 and a second end 38. Moving from the first end 37 toward the second end 38, the releasing mechanism 12 has a release button 30. As best shown in FIGS. 10 and 11, the release button 30 has a hollow shaft 78 and a head 67. The head 67 has a larger diameter than the shaft 78. Recesses 79 that extend toward the second end 38 are formed at the first end 37 on the head 67. A screw receiving recess 40 extends from the first end 37 though the head 67 and the shaft 78. The shaft 78 has projections 71 that extend toward the second end 38.

Figure 13A:
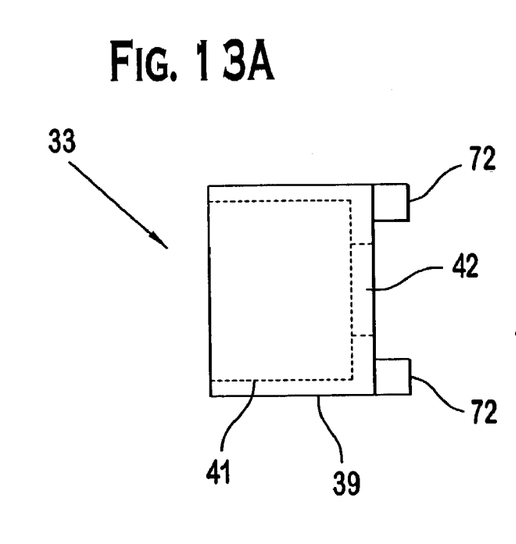
FIG. 13A is a side view of the cover of the prosthetic attachment locking device.
Figure 13B:
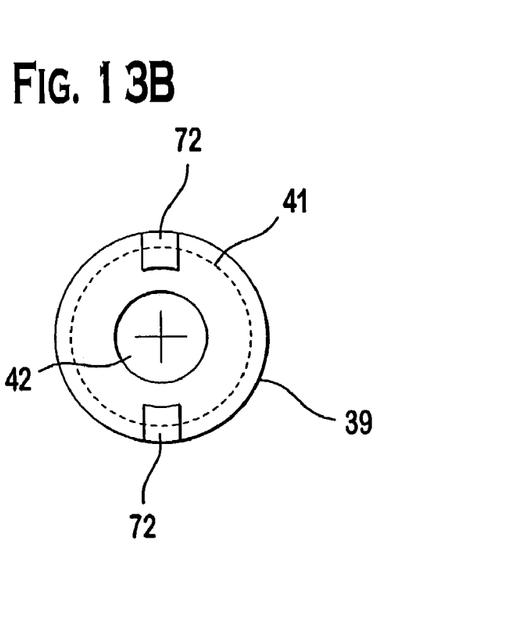
FIG. 13B is a bottom view of FIG. 13A.

As shown in FIG. 9, the shaft 78 is encompassed by a spring 32. The spring 32 is encompassed by a cover 33. As shown in FIG. 13, the cover 33 has an outer cover surface 39 that has a larger diameter than the release button 30 of the head 67. The cover 33 has an inner cover surface 41 having an axle receiving aperture 42. Locking projections 72 extend from the outer cover surface 39 toward the second end 38.

Figure 14:
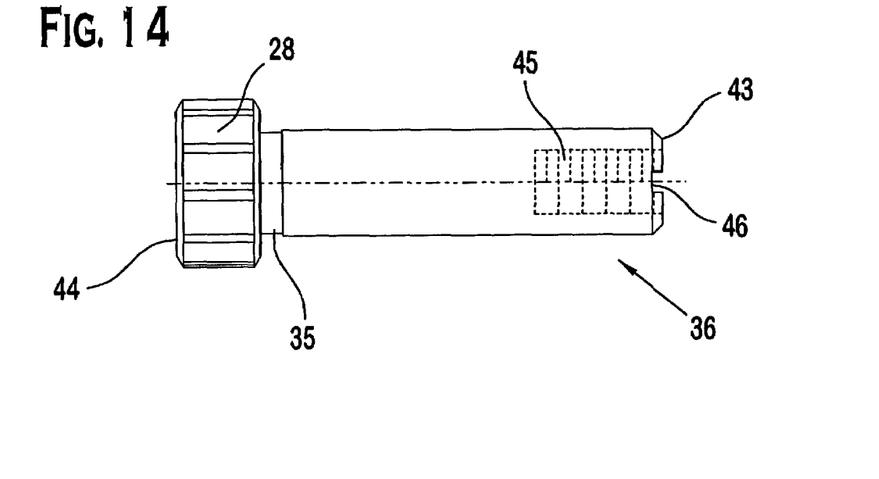
FIG. 14 is a side view a pawl attached to a central axle of the prosthetic attachment locking device.
Figure 15:
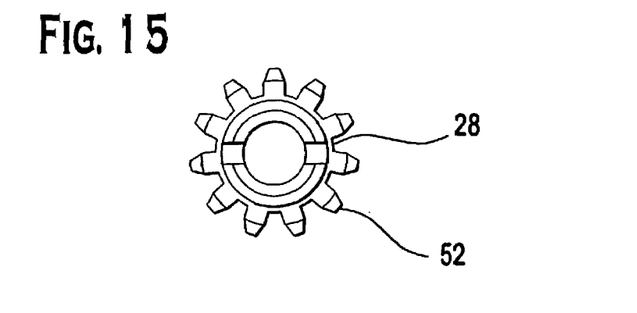
FIG. 15 is a top view of the pawl of the prosthetic attachment locking device.
Figure 17A:
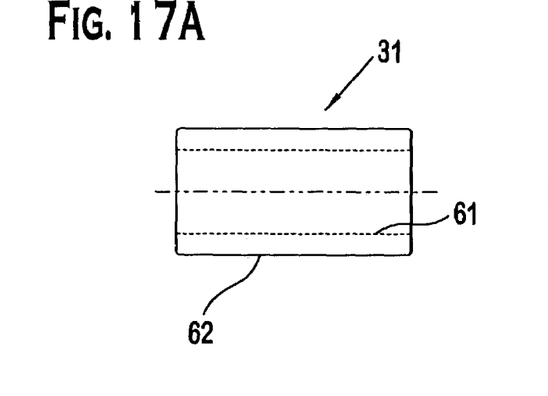
FIG. 17A is a side view of the clutch bearing of the prosthetic attachment locking device.
Figure 17B:
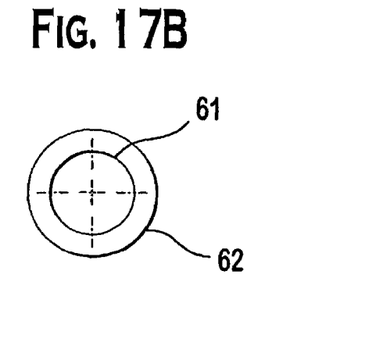
FIG. 17B is a top view of FIG. 17A.
Figure 18A:
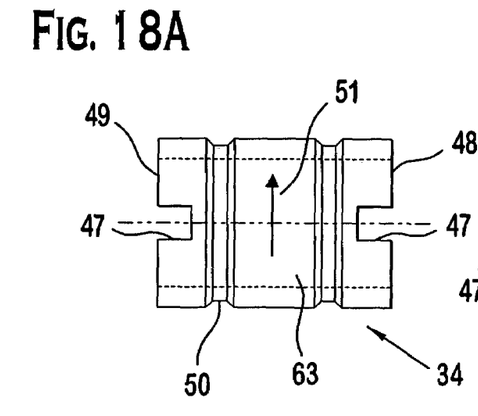
FIG. 18A is a side view of the sleeve of the prosthetic attachment locking device.
Figure 18B:
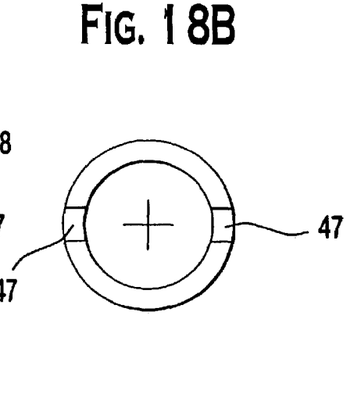
FIG. 18B is a top view of FIG. 18A.

As shown in FIG. 9, adjacent the cover 33 is a central axle 36. The central axle 36 has an attachment end 43 and a pawl end 44, as shown in FIG. 14. The attachment end 43 is positioned toward the first end 37 and has a screw aperture 45 and shaft projection receiving recesses 46. As shown in FIG. 17, a clutch bearing 31 encompasses the central axle 36 and has inner and outer bearing surfaces 61, 62, respectively. The inner bearing surface 61 has a plurality of projections (not shown) that only enable the clutch bearing 31 to rotate about the central axle 36 in a first direction. Encasing the outer bearing surface 62 is a sleeve 34, as best shown in FIG. 18. The sleeve 34 has locking projection receiving recesses 47 on a first sleeve end 48 and a second sleeve end 49. An arrow 51 on an outer sleeve surface 63 designates the first direction that the clutch bearing 31 is able to rotate with respect to the central axle 36. Ball plunger receiving grooves 50 circumscribe the outer sleeve surface 63. As shown in FIG. 14, adjacent the clutch bearing 31 and positioned at the pawl end 44 of the central axle 36 is a spacer 35. The spacer 35 may be made out of any suitable material such as plastic. Adjacent the spacer 35 and attached to the pawl end 44 of the central axle 36 is a pawl 28. As shown in FIG. 15, the pawl 28 has a plurality of teeth 52 for engaging the attachment pin 13.

The attachment pin 13 will now be described in greater detail. As shown in FIG. 1, the attachment pin 13 has a substantially elongated pin body 55 having a lip 56 and a pin head 57. The pin body 55 has a plurality of ratcheted teeth 68 that extend the length of the pin body 55. The pin head 57 has a larger diameter then the pin body 55. The lip 56 has a larger diameter then the pin head 57 and is positioned between the pin head 57 and the pin body 55.

Figure 19A:
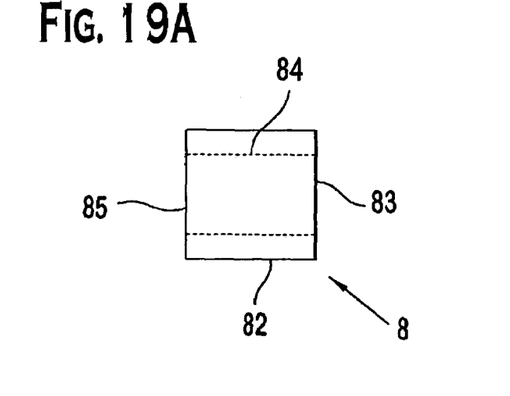
FIG. 19A is a side view of the hollow cylindrical spacer.
Figure 19B:
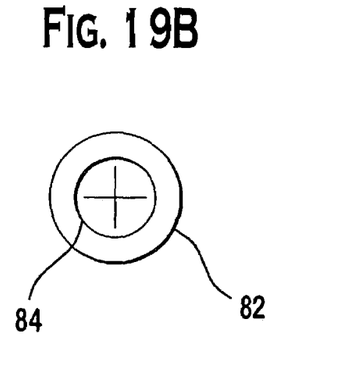
FIG. 19B is a top view of FIG. 19A.

The hollow cylindrical spacers 19 will now be described in greater detail. As shown in FIG. 19, the hollow cylindrical spacers 8 have first and second edges 83, 85 and inside and outside surfaces 84, 82, respectively. The outside surface 84 has a diameter substantially similar to a diameter of the hollow cylinder receiving recesses 19. The inside surface has a diameter substantially similar to a diameter of the second set of apertures 18.

Figure 2:
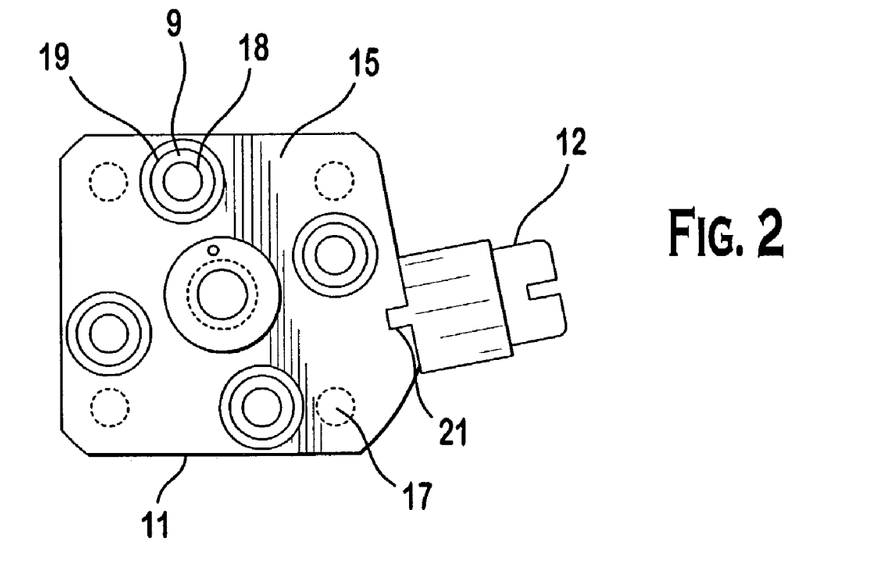
FIG. 2 is a top plan view of the prosthetic attachment locking device assembled for attachment with a right-side residual limb.

The assembly of the prosthetic attachment locking device 10 for use with a right-side residual limb will now be described in greater detail with reference to FIGS. 1 and 2. As shown in FIGS. 1 and 2, the bushing 70 is inserted into the axial hole 16 until the flange 53 is adjacent to the second surface 15 of the body 11. The bushing 70 is inserted such that the dowel pin 74 is received in the dowel pin hole 20, positioning the radial hole 54 adjacent to the slot 25.

As shown in FIGS. 9 and 18, the releasing mechanism 12 is assembled by inserting the clutch bearing 31 having the sleeve 34 onto the central axle 36 such that the second sleeve end 49 is adjacent to the spacer 35. The attachment end 43 of the central axle 36 is received in the axle receiving aperture 42 of the cover 33 such that the locking projections 72 are received in the locking projection receiving recesses 47 of the first sleeve end 48. The spring 32 is positioned over the shaft 78 of the release button 30. The shaft 78 bearing the spring 32 is received in the cover 33 such that an end of the spring 32 surrounds the attachment end 43 of the central axle 36 and the projections 71 of the shaft 78 are received in the shaft projection receiving recesses 46. A screw 29 is then received in the screw receiving recess 40 and is tightened by a means such as a hex key, fastening the release button 30 to the attachment end 43 of the central axle 36.

The second end 38 of the releasing mechanism 12 is received in the sleeve receiving recess 23 until the pawl 28 is received in the pawl receiving recess 24 and communicates with the slot 25. In this position, the ball 60 is received in the ball plunger receiving grooves 50 on the sleeve 34. The locking projections of the cover 33 are received in the locking recesses 21 formed on the first and second surfaces 14, 15 of the body 11, locking the releasing mechanism 12 in position. The second surface 15 of the body 11 is then positioned under the right-side residual limb (not shown) such that the releasing mechanism 12 projects from the prosthetic attachment locking device 10 toward the interior of the residual limb.

Figure 20:
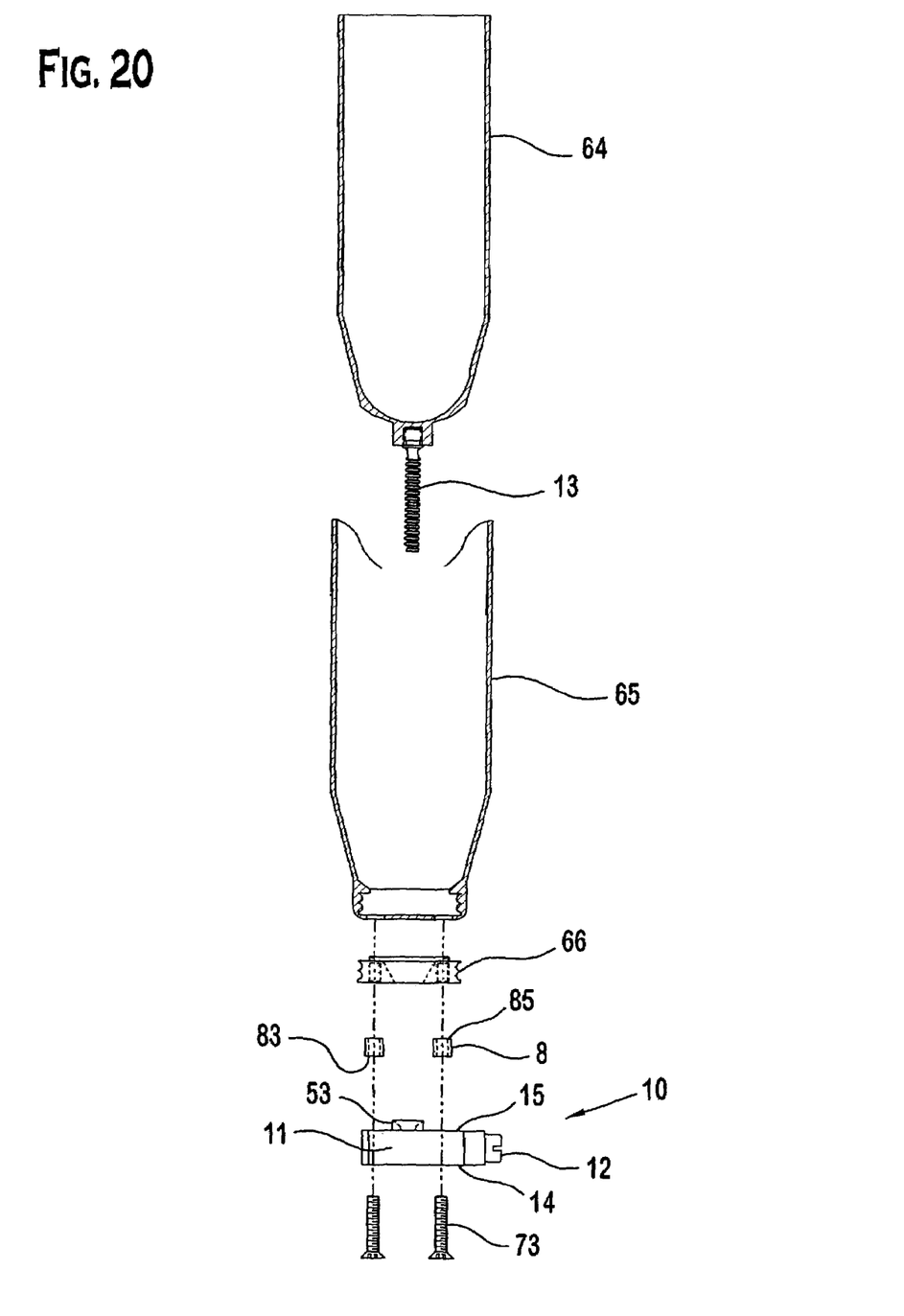
FIG. 20 is a schematic view of the assembly of the prosthetic attachment locking device with a prosthetic socket and liner positioned for attachment to a right-side residual limb.
Figure 21:
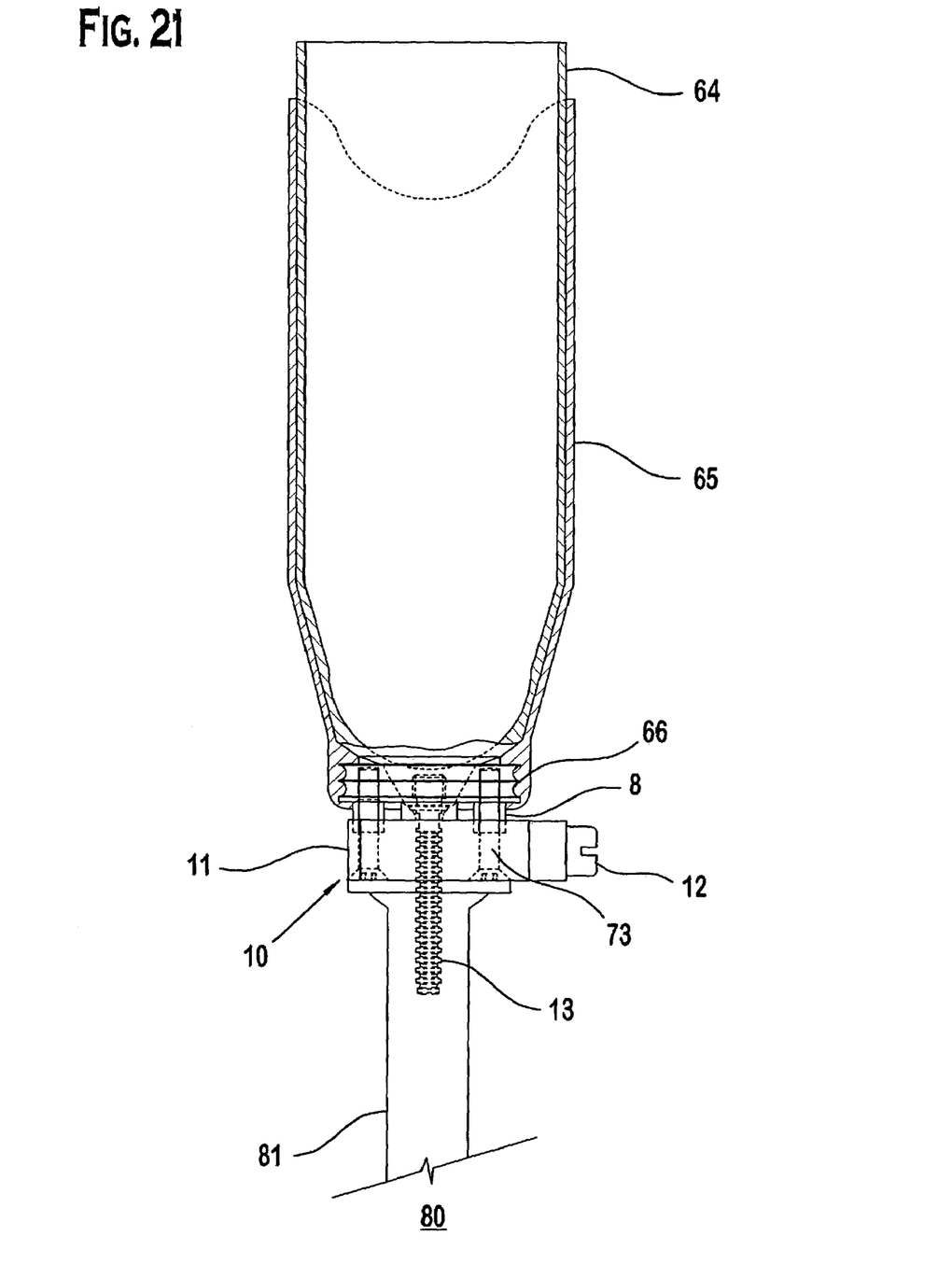
FIG. 21 is a front plan view of the assembled prosthetic attachment locking device attached to the right-side residual limb.

Attachment of a prosthetic socket 65 and liner 64 for a right-side residual limb (not shown) to a pylon 81 of a prosthetic limb 80 with the prosthetic attachment locking device 10 will now be described in greater detail. As shown in FIGS. 20 and 21, a first edge 83 of the hollow cylindrical spacers 8 is positioned adjacent to the bottom surface 9 of the second surface 15 of the body 11 in the hollow cylinder receiving recesses 19 of the second set of apertures 18. A socket 65 having a laminated ring 66 is positioned adjacent to the second edge 85 of the hollow cylindrical spacers 8. Socket screws 73 are received in the second set of apertures 18. The socket crews 73 are inserted from the first surface 14 of the body 11 and extend through the body 11, the inside surface 84 of the hollow cylindrical spacers 8 and into the laminated ring 66. The pin body 55 of the attachment pin 13 that extends distally from the liner 64 is inserted into the socket 65 such that the pin body 55 extends through the laminated ring 66 and is received in the flange 53 of the bushing 70. The ratcheted teeth 68 of the attachment pin 13 engage the pawl 28 causing the pawl 28 and the clutch bearing 31 to rotate in the first direction shown by the arrow 51 in FIG. 18A. As the pawl 28 rotates, the ball 60 rotates within the ball plunger receiving groove 50 on the sleeve 34. The attachment pin 13 is inserted until the lip 56 of the attachment pin 13 is adjacent to the bushing 70 and a distal end of the attachment pin 13 is received in the pylon 81 of the prosthetic limb (not shown) to secure the residual limb (not shown) to the prosthetic limb 80.

To detach the residual limb (not shown) from the prosthetic limb 80, the head 67 of the release button 30 is pressed toward the body 11. As the head 67 is received in the inner cover surface 41, the head 67 pushes against a biasing force of the spring 32 such that the shaft 78 presses against the attachment end 43 of the central axle 36, displacing the pawl 28 beyond the slot 25 and the ratcheted teeth 68 of the attachment pin 13. The ball 60 retained in the ball plunger receiving groove 50 holds the sleeve 34 and the clutch bearing 31 in position while the central axle 36 and pawl 28 are displaced by the spring 32. The attachment pin 13 is released from the pawl 28 and resultantly may be removed from the axial hole 16. After the attachment pin 13 is removed, the releasing mechanism 12 may be removed from the body 11 by pulling the releasing mechanism 12 away from the first side 22.

Figure 4:
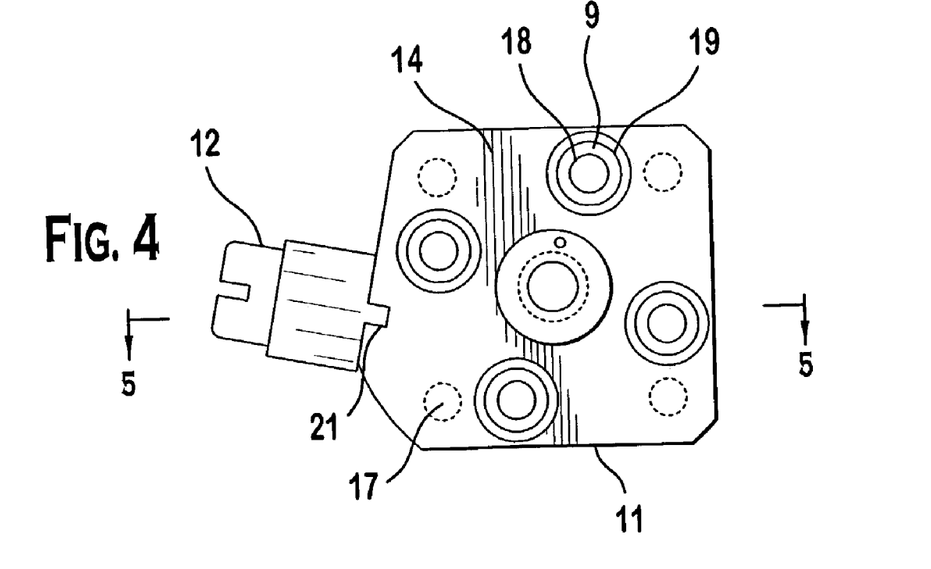
FIG. 4 is a top plan view of the prosthetic attachment locking device assembled for attachment with a left-side residual limb.

The assembly of the prosthetic attachment locking device 10 for use with a left-side residual limb will now be described in greater detail with reference to FIGS. 3 and 4. The bushing 70 is inserted into the axial hole 16 until the flange 53 is adjacent to the first surface 14 of the body 11. The bushing 70 is inserted such that the dowel pin 74 is received in the dowel pin hole 20, positioning the radial hole 54 adjacent to the slot 25.

As shown in FIGS. 9 and 18, the releasing mechanism 12 is assembled by inserting the clutch bearing 31 having a sleeve 34 onto the central axle 36 such that the first sleeve end 48 is adjacent to the spacer 35. The attachment end 43 of the central axle 36 is received in the axle receiving aperture 42 of the cover 33 such that the locking projections 72 are received in the locking projection receiving recesses 47 of the second sleeve end 49. The spring 32 is positioned over the shaft 78 of the release button 30. The shaft 78 bearing the spring 32 is received in the cover 33 such that an end of the spring 32 surrounds the attachment end 43 of the central axle 36 and the projections 71 of the shaft 78 are received in the shaft projection receiving recesses 46. A screw 29 is then received in the screw receiving recess 40 and is tightened by a means such as a hex key, fastening the release button 30 to the attachment end 43 of the central axle 36.

The second end 38 of the releasing mechanism 12 is received in the sleeve receiving recess 23 until the pawl 28 is received in the pawl receiving recess 24 and communicates with the slot 25. In this position, the ball 60 is received in the ball plunger receiving grooves 50 on the sleeve 34. The locking projections of the cover 33 are received in the locking recesses 21 formed on the first and second surfaces 14, 15 of the body 11, locking the releasing mechanism 12 in position. The first surface 14 of the body 11 is then positioned under the left-side residual limb (not shown) such that the releasing mechanism 12 projects from the prosthetic attachment locking device 10 toward the interior of the residual limb.

Figure 22:
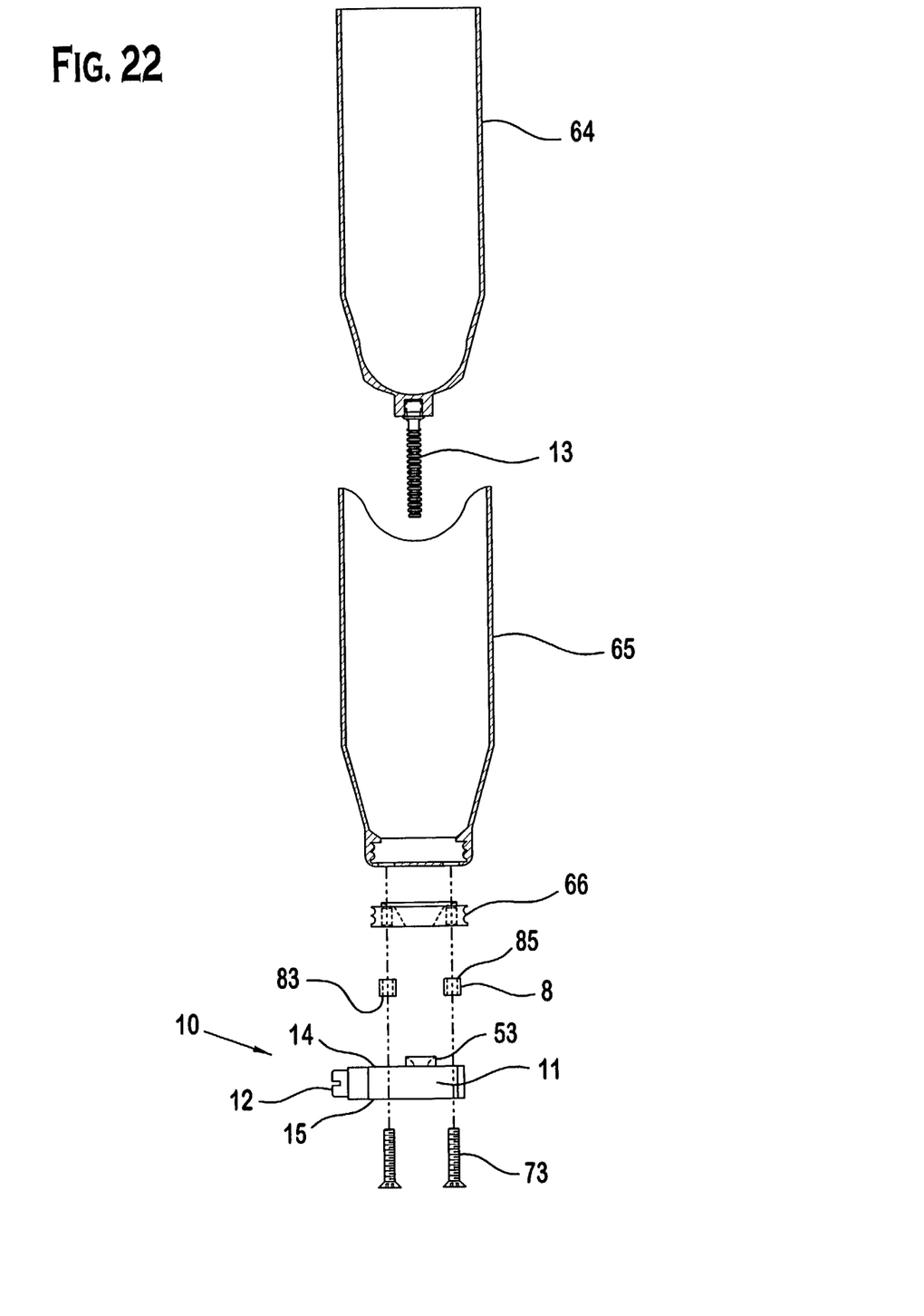
FIG. 22 is a schematic view of the assembly of the prosthetic attachment locking device with a prosthetic socket and liner positioned for attachment to a left-side residual limb.

Attachment of a prosthetic socket 65 and liner 64 for a left-side residual limb (not shown) to a pylon 81 of a prosthetic limb 80 with the prosthetic attachment locking device 10 is substantially similar to the method of attachment previously described for a right-side residual limb (not shown). As shown in FIG. 22, for attachment to a left-side residual limb (not shown), the first edge 83 of the hollow cylindrical spacers 8 is positioned adjacent to the bottom surface 9 of the first surface 14 of the body 11 in the hollow cylinder receiving recess 19 of the second set of apertures 18. The socket 65 having a laminated ring 66 is positioned adjacent to the second edge 85 of the hollow cylindrical spacers 8. The socket screws 73 are received in the second set of apertures 18 from the second surface 15 of the body 11 and extend through the body 11, the inside surface 84 of the hollow cylindrical spacers 8 and into the laminated ring 66. The attachment pin 13 extends distally from a liner 64 and the pin body 55 is inserted into the socket 65. The pin body 55 extends through the laminated ring 66 and is received in the flange 53 of the bushing 70. The ratcheted teeth 68 of the attachment pin 13 engage the pawl 28 causing the pawl 28 and the clutch bearing 31 to rotate in the first direction shown by the arrow 51 in FIG. 18A. As the pawl 28 rotates, the ball 60 rotates within the ball plunger receiving groove 50 on the sleeve 34. The attachment pin 13 is inserted until the lip 56 of the attachment pin 13 is adjacent to the bushing 70 and a distal end of the attachment pin 13 is received in the pylon 81 of the prosthetic limb (not shown) to secure the residual limb (not shown) to the prosthetic limb 80.

To detach the residual limb (not shown) from the prosthetic limb 80, the head 67 of the release button 30 is pressed toward the body 11. As the head 67 is received in the inner cover surface 41, the head 67 pushes against a biasing force of the spring 32 such that the shaft 78 presses against the attachment end 43 of the central axle 36, displacing the pawl 28 beyond the slot 25 and the ratcheted teeth 68 of the attachment pin 13. The ball 60 retained in the ball plunger receiving groove 50 holds the sleeve 34 and the clutch bearing 31 in position while the central axle 36 and pawl 28 are displaced by the spring 32. The attachment pin 13 is released from the pawl 28 and resultantly can be removed from the axial hole 16. After the attachment pin 13 is removed, the releasing mechanism 12 can be removed from the body 11 by pulling the releasing mechanism 12 away from the first side 22.

Because the releasing mechanism 12 has a reversible clutch bearing 31, the prosthetic attachment locking device 10 is reversible in that the releasing mechanism 12 can project toward the interior of the residual limb (not shown) whether used on a right-side residual limb or a left-side residual limb. The combination of locking projections on the releasing mechanism 12 secures the releasing mechanism 12 in the body 11 to maintain the attachment pin 13 in an attached state. The positioning of the hollow cylindrical spacers 8 on the bottom surfaces 9 of the second set of apertures 18 enables torque caused by irregularity in the socket attachment surface to be evenly distributed between the socket 65 and the prosthetic attachment locking device 10.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A prosthetic attachment locking device, comprising:
    a body having an axial hole that extends from a first surface to an opposing second surface, the body having a first side with a pawl receiving recess that communicates with the axial hole; and
    a releasing mechanism having a central axle with a pawl that is received in the pawl receiving recess, the central axle having a clutch bearing that rotates the pawl in a first direction when an attachment pin is inserted into the axial hole and engages the pawl, the clutch bearing secures the attachment pin in the body and is reversible such that an attachment pin can be inserted from the first surface or the second surface of the body, the clutch bearing is reversible after the releasing mechanism has been assembled.

2. The device of claim 1, wherein the releasing mechanism can be positioned to project from the base toward an interior of a right-side residual limb between the right-side residual limb and a left-side limb when the attachment pin is inserted in the second surface and toward an interior of a left-side residual limb between the left-side residual limb and a right-side limb when the attachment pin is inserted in the first surface.

3. The device of claim 1, wherein the releasing mechanism includes a release button and a spring, the release button pushes against a biasing force of the spring to displace the pawl from the axial hole such that the attachment pin can be removed from the axial hole.

4. The device of claim 3, wherein the release button includes a shaft with a projection that engages a shaft projection receiving recess on the central axle to secure the release button to the central axle.

5. The device of claim 3, wherein the releasing mechanism includes a screw that attaches the release button to the central axle.

6. The device of claim 3, wherein the release button has a cover with locking projections that engage a first locking recess formed on the base to secure the releasing mechanism within the base.

7. The device of claim 6, wherein the clutch bearing includes a sleeve with a second locking recess that engages the locking projections to secure the releasing mechanism within the base.

8. The device of claim 7, wherein the sleeve has second locking recesses on both ends thereof so that the clutch bearing is secured by the locking projections when the clutch bearing is reversed.

9. The device of claim 1, wherein the releasing mechanism includes a spacer positioned between the clutch bearing and the pawl.

10. The device of claim 1, wherein the clutch bearing is encased by a sleeve.

11. The device of claim 1, wherein the base is provided with a ball plunger, the ball plunger engages with ball plunger receiving grooves on an outer surface of the releasing mechanism to secure the releasing mechanism within the base.

12. The device of claim 1, wherein the body has a plurality of apertures extending from the first surface to the second surface, the apertures having a recessed portion on the first surface and the second surface with an essentially flat bottom surface for receiving hollow cylindrical spacers positioned between the body and a prosthetic socket to evenly distribute torque between the prosthetic socket and the body.

13. The device of claim 1, further comprising a removable bushing that is received in the axial hole, the bushing has an outwardly extending flange for guiding the attachment pin into the axial hole.

14. The device of claim 13, wherein the flange includes a dowel pin that extends toward the body, the dowel pin corresponds with a radial hole in the bushing and is received in a dowel pin hole in the body to ensure the radial hole is aligned with the pawl receiving recess where it communicates with the axial hole.

15. The device of claim 1, wherein the body and the releasing mechanism are made from a high strength aluminum alloy.

16. A prosthetic attachment locking device, comprising:
a body having a first locking recess formed adjacent to a sleeve receiving recess;
a releasing mechanism having a central axle with a pawl, the central axle having a clutch bearing for rotating the pawl in a first direction, a sleeve having a second locking recess encases the clutch bearing; and
a release button attached to the central axle having a cover with locking projections that are received in the first and second locking recesses to secure the releasing mechanism within the sleeve receiving recess.

17. The device of claim 16, wherein the clutch bearing is reversible and the sleeve has second locking recesses on both ends thereof so that the clutch bearing is secured by the locking projections when the clutch bearing is reversed.

18. The device of claim 16, wherein the base is provided with a ball plunger, the ball plunger engages with ball plunger receiving grooves on an outer surface of the sleeve to secure the releasing mechanism in the base.

19. The device of claim 16, wherein the releasing mechanism includes a screw that attaches the release button to the central axle.

20. The device of claim 16, wherein the body has a plurality of apertures extending from a first surface to a second surface, the apertures having a recessed portion with an essentially flat bottom surface for receiving hollow cylindrical spacers positioned between the body and a prosthetic socket to evenly distribute torque between the prosthetic socket and the body.

21. The device of claim 16, wherein the release button includes a shaft with a projection that engages a shaft projection receiving recess on the central axle to secure the release button to the central axle.

* * * * *